United States Patent [19]

Gomberg

[11] Patent Number: 4,864,142
[45] Date of Patent: Sep. 5, 1989

[54] METHOD AND APPARATUS FOR THE NONINVASIVE INTERROGATION OF OBJECTS

[75] Inventor: Henry J. Gomberg, Ann Arbor, Mich.

[73] Assignee: Penetron, Inc., Ann Arbor, Mich.

[21] Appl. No.: 142,810

[22] Filed: Jan. 11, 1988

[51] Int. Cl.[4] .............................................. G01N 23/20
[52] U.S. Cl. ......................... 250/390.04; 250/390.07; 250/390.02; 378/57
[58] Field of Search ............. 250/390 C, 493.1, 496.1, 250/269, 390 F, 390 I, 390 K, 390 A; 378/57

[56] References Cited

U.S. PATENT DOCUMENTS

| | | | |
|---|---|---|---|
| 2,567,057 | 9/1951 | Crumrine | 250/390 C |
| 3,146,349 | 8/1964 | Jordan | 250/390 C |
| 3,832,545 | 8/1974 | Bartko | 378/57 |
| 3,997,787 | 12/1976 | Fearon | 250/390 C |
| 4,251,726 | 2/1981 | Alvarez | 250/390 C |
| 4,539,648 | 9/1985 | Schatzki | 378/57 |

FOREIGN PATENT DOCUMENTS

| | | | |
|---|---|---|---|
| 2150737 | 7/1985 | United Kingdom | 250/493.1 |
| 2151837 | 7/1985 | United Kingdom | 250/493.1 |

OTHER PUBLICATIONS

Schrack et al., "Nuclear Fuel Assay Using Resonance Neutrons", *Dimensions NBS,* vol. 64, No. 4, May/Jun. 1980, pp. 21–23.

*Primary Examiner*—Janice A. Howell
*Assistant Examiner*—William F. Rauchholz
*Attorney, Agent, or Firm*—Krass & Young

[57] ABSTRACT

Neutron elastic scatter resonance is employed for the noninvasive interrogation of objects as for example to detect explosives and narcotics in closed containers. A resonant scattering spectrum of the object is obtained by projecting a collimated, monoenergetic beam of neutrons onto the object, varying the energy of the beam and measuring the scattered neutrons as a function of the beam energy. The thus generated spectra and analyzed so as to determine either the pressence of particular elements of interest or the relative ratios of those elements. Ratios so determined may be compared with corresponding ratios established for contraband items. If the ratios fall within the range for contraband, an alarm indication is provided. The present invention provides method and apparatus for contraband detection.

49 Claims, 5 Drawing Sheets

METHOD AND APPARATUS FOR THE NONINVASIVE INTERROGATION OF OBJECTS

FIELD OF THE INVENTION

This invention relates to methods and apparatus for noninvasively assessing the composition or contents of objects such as closed or otherwise inaccessible containers. In particular, the present invention relates to a method and apparatus for detecting materials such as hazardous substances or other contraband by employing resonantly scattered neutrons to effect such inspection.

BACKGROUND OF THE INVENTION

The need for rapid, safe and non-intrusive inspection systems has been increasing greatly. Typical of this need is the necessity of inspecting parcels and packages at transport terminals, post offices and freight depots.

The cost of international travel has decreased significantly recent years and with this decrease there has been a dramatic increase in the volume of international passengers. Concomitant with this increase in the number of travelers has been an increase in the smuggling of contraband via commercial carriers. By contraband it is meant any substance whose trade or transport is restricted by law. As used specifically herein contraband shall refer primarily to hazardous materials such as explosives and narcotics, and shall include military explosives such as mines and ammunition disposed in vehicles, buildings, packages or atop or beneath the surface of the earth.

Because of an increasing demand for narcotics and because of increasing world tension there has been a significant escalation in the transport of such contraband across international borders. It is desirable to interdict such commerce, but because of the greatly increased volume of international traffic, such interdiction becomes very difficult.

While it is theoretically possible to inspect every parcel or item of baggage passing across a border, through an air, rail or sea terminal or through a post office, such inspection would be very costly in terms of wasted time and impeded commerce; furthermore, smugglers frequently resort to the use of packages having hidden compartments, false bottoms and the like which may be overlooked in all but the most scrupulous inspection.

Also, there is a need for explosive detection techniques which may be adapted to quickly scan the surface or subsurface of the earth for mines or other buried explosives. It is preferred that such technique be reliable, rapid and capable of conducting such inspection from a distance, as for example in a fly-over inspection.

Accordingly, there is a need for a rapid method for detecting the presence of contraband and it is preferred that the technique be noninvasive or nonvisual, that is to say be capable of inspecting the contents of a closed container, without necessitating opening of the container. In many instances a container will not be "closed" in the sense of being sealed, but may be partially opened, porous or permeable; however, as used herein a closed container shall include all such containers not readily subject to visual inspection and shall include parcels, packages, and envelopes as well as structural components of buildings and vehicles. In some instances mines or other military explosives are disposed beneath the soil or waters of the earth's surface, whereas in other instances such devices are "laid" upon the surface of the earth and rely upon camouflage or natural cover to hide them. Therefore, for purposes of this disclosure such devices shall also be deemed to be enclosed.

Such a noninvasive method would save time as well as be highly accurate insofar as false bottoms and the like would not present a source of confusion. It is required that any such inspection technique not harm the articles being inspected or present any lingering physical hazards to the owners of the articles.

Magnetic techniques are employed for the detection of metallic articles such as weapons however, nonmetallic items such as explosives or narcotics are not detected by such techniques. X-ray inspection is frequently employed to view the contents of closed packages, but cannot identify the composition of the observed materials. Many explosives and narcotics have unremarkable x-ray absorption characteristics and hence are indistinguishable from more normal items of commerce. Therefore it may be seen that heretofore employed magnetic or X-ray techniques cannot detect many items of contraband.

The use of neutrons for analysis of the contents of closed packages has previously been investigated. Thermal neutron activation analysis (TNAA) is an analytical technique which has been known and utilized for some time to perform quantitative and qualitative analyses. In this technique relatively low energy neutrons are employed to bombard a sample under investigation. The nuclei of component atoms thereof capture these neutrons and become radioactive. These newly formed radioactive isotopes then undergo atomic decay and emit energetic particles and/or photons in the process. By identifying the emitted radiation, the composition of the sample may be determined. While TNAA techniques are capable of identifying various chemical elements they are not well suited for the high volume inspection of closed containers, as for example at airport terminals, border stations, post offices and the like. TNAA of necessity renders a sample being inspected radioactive and this radioactivity may persist for a significant period of time after completion of analysis thereby presenting a potential health hazard. In many instances, the exact composition of the sample under investigation is not known and consequently the duration of the induced radiation cannot be told beforehand. Thus many inspected items will have the potential of remaining radioactive for fairly long periods of time. Furthermore, TNAA techniques are not particularly efficient for detecting nitrogen or carbon, major components of narcotics and explosives, because the capture cross section for these elements is quite small as compared to that of metals and other heavy elements. Consequently if a usable signal is to be produced, a relatively high neutron flux must be employed, and this high flux can induce significant residual radioactivity in objects being inspected. Additionally, TNAA is very insensitive to oxygen, another element of interest in narcotics and explosives.

Neutron absorption analysis is another technique proposed for the noninvasive inspection of closed containers. In such a process, the absorption of high energy neutrons as they pass through an object is measured. Certain elements are very strongly absorbing of neutrons whereas others are not and this absorption may be utilized to characterize a sample. For example, neutron absorption techniques may be utilized to look for nitrogen or other elements typically associated with narcotics or explosives. The main problem with neutron absorption analysis is that there are a number of elements having very strong absorption signatures which interfere with the detection of the element of interest. For example, boron, as well as various rare earth elements have significant neutron absorptions which can mask or otherwise interfere with the absorption of neutrons by nitrogen. Additionally, the absorption of neutrons can create the aforementioned problems of lingering radioactivity.

U.S. Pat. No. 3,997,787 discloses a dual stage analysis system for the detection of explosives in closed packages. The system relies upon the use of thermal neutron activation to detect the presence of oxygen in the contents of the container and neutron absorption to detect the presence of nitrogen therein. The presence of significant quantities of both elements is taken as an indication that explosives may be present in the container. The method of U.S. Pat. No. 3,997,787 suffers from the aforementioned shortcomings of both neutron absorption and neutron activation techniques.

In accord with the present invention it has been found that the resonant elastic scattering of neutrons may be employed with advantage in the detection of contraband in closed containers. Resonant elastic scattering is a process whereby neutrons impinge upon and are scattered with minimum energy loss from the nuclei of target atoms. The scattering is typically isotropic insofar as the neutrons are uniformly scattered in all directions from the target nucleus. In those instances where resonant scattering of neutrons is backwards in the general direction of the source, the technique is referred to as back scattering. Since the scattering is elastic no residual radioactivity is created in the target atom. Neutron resonant elastic scattering also has a further advantage in relation to neutron absorption or activation techniques and that is due to the fact that the elastic scattering cross section for neutrons is much larger than the absorption cross section and this difference is greatest for the light elements where scattering cross sections are typically 100 to 1000 times greater than absorption cross sections. Such large cross sections make possible the use of relatively low fluxes of neutrons for resonant elastic scattering analyses.

Neutron resonant elastic scattering techniques are also highly specific for particular elements. That is to say each element has a unique elastic scattering spectrum characterized by the presence of resonance peaks therein, said peaks representing particular neutron energies at which the elastic scattering cross section of a given element is large. Resonance spectra may be readily measured by varying the energy of a monochromatic neutron beam and measuring the intensity of elastically scattered neutrons as a function of beam energy. It should be noted that by the term "monochromatic" is meant a beam having a relatively narrow distribution of energies, analogous to a beam of light of a single wavelength; such a beam may also be referred to as "monoenergetic." As will be explained in greater detail hereinbelow, resonant elastic scattering techniques form the basis for a highly specific and accurate analytical system adapted for the non-invasive interrogation of objects, such as objects which are buried or in closed containers.

Each element has a particular neutron elastic scatter spectrum characterized by a number of particular resonance peaks which can be used to establish the presence of and/or quantify the amount of that particular element present. Likewise, a particular chemical compound will have a unique neutron scatter spectrum reflecting the relative percent of the various component atoms thereof. Contraband items it will thus be appreciated will each present a unique neutron resonant elastic scatter spectrum.

Even more significantly various classes of contraband or other hazardous items will be characterized by certain common features in their resonant scatter spectra, reflecting certain ranges or proportions of various component atoms. For example, explosives broadly fall into two common classes. The first class is referred to as "oxidizing explosives" and its members derive their power from the very rapid oxidation of carbon and hydrogen. Nitrates are the most effective fast acting sources of oxygen for such reactions. Oxidizing explosives are characterized by an oxygen-nitrogen ratio which may range from 1 to 4. Some oxidizing explosives are listed in Table 1 below.

TABLE 1

| Oxidizing Explosive | Atomic Ratios | | |
|---|---|---|---|
| | H:N | O:N | C:N |
| Ammonium Nitrate $NH_4NO_3$ | 2.0 | 1.5 | 0 |
| Nitroglycerin $C_3H_5N_3O_9$ | 1.67 | 3 | 1 |
| Nitromethane $CH_3NO_2$ | 3 | 2 | 1 |
| Tetranitromethane $C(NO_2)_4$ | 0 | 2 | 0.25 |
| RDX $C_3H_6N_6O_6$ | 1 | 1 | 0.5 |
| Tetryl $C_6H_5N_5O_8$ | 1 | 1.6 | 1.2 |

A second class of commonly employed explosives derives its power from the high energy disassociation of metastable, oxygen-free nitrogen compounds such as azides. In such explosives, the oxygen-nitrogen ratio is generally 0, the hydrogen-nitrogen ratio is 1 or less and the carbon-nitrogen ratio is lower. Some such explosives are listed in Table 2.

TABLE 2

| Dissociating Explosives | Atomic Ratios | |
|---|---|---|
| | H:N | C:N |
| Hydrazine Azide $N_2H_4HN_3$ | 1 | 0 |
| Guanyl Azide $CH_6N_4$ | 1.5 | 0.25 |
| Tetrazene $CH_7N_9O$ | 0.78 | .11 |

Reference to the ratios listed in the tables above indicates that specific compositional ranges may be associated with specific types of contraband explosives. By reference to a plurality of such compositional ranges false readings which could stem from looking at the ratio of a single pair of elements would be eliminated. For example, acrylonitrile, the basic component of commercial plastics such as Orlon has a carbon-nitrogen of three and hydrogen-nitrogen ratio of three. Based upon a simple analysis for the presence of nitrogen Orlon might be mistaken for an explosive compound. However, the oxygen-nitrogen ratio of acrylonitrile is 0 therefore it can be eliminated as being an oxidizing type explosive. Furthermore, the hydrogen-nitrogen ratio is three, whereas typical disassociating type explosives have a lower hydrogen-nitrogen ratio therefore acrylonitrile can be disqualified as being a dissociating type explosive. Melamine, another common plastic has an empirical formula of $C_3H_6N_6$. Consequently, H:N ratio is 1 and its C:N ration is 0.5. This might allow it to be confused with RDX; however, the O:N ratio is 0, therefore melamine can be readily distinguished from such explosives.

Neutron resonant scatter analysis enables one to rapidly and reliably obtain a plurality of ratios of elements in a sample and, since what is being measured are ratios and not absolute quantities, the process is effectively "self-standardizing."

Similar ratios may be established for narcotic contraband. Referring now to Table 3, there are shown elemental ratios for particular narcotics.

TABLE 3

| Narcotics | Atomic Ratios | | |
|---|---|---|---|
| | H:N | C:N | O:N |
| Morphine | 19 | 17 | 3 |
| Cocaine | 21 | 17 | 4 |
| Heroin | 23 | 21 | 5 |
| Methadone | 27 | 21 | 1 |
| Codeine | 23 | 18 | 3 |

It will be seen that there are particular atomic ratios associated with narcotic materials. Referring now to Table 4, there are shown atomic ratios for various articles of commerce which may be expected to be found in luggage, parcels or the like.

TABLE 4

| Articles of Commerce | Atomic Ratios | | |
|---|---|---|---|
| | H:N | C:N | O:N |
| Wool | 4.8 | 3.3 | 1.1 |
| Silk | 4.5 | 3.0 | 1.2 |
| Leather | 4.8 | 3.1 | 1.3 |
| Acrylonitrile | 3+ | 3+ | 0 |

It is apparent then that there are distinct groups of atomic ratios associated with explosives, narcotics and innocuous materials and these ratios may be utilized as a basis for the determination of the presence of contraband in a container without the need for the visual inspection thereof.

In addition to the use of a ratio-type analysis, neutron resonant scatter analysis may also be employed to simply determine the presence or absence of particular elements which may be expected to occur in contraband materials. For example, nitrogen is present in virtually all explosives, while mercury, lead or other heavy metals are frequently found in explosive primers. Similarly, sulfur, phosphorous and potassium are frequently found in black powder explosives and elements such as boron and beryillium are present in nuclear devices; thus the presence of such atomic species may be indicative of the presence of explosive contraband.

In an embodiment of this type, a single resonance peak or group of peaks characteristic of a given element is scanned for. Magnitude of the peak will give some information regarding quantities of the species of interest. This single element embodiment is well suited for simple, rapid scanning, and may be used to "pre-screen" items prior to implementing a full ratio type scan.

The neutron resonant scatter analysis techniques of the present invention confer significant advantage in the detection of contraband material insofar as such materials may be reliably detected in the presence of relatively large amounts of innocuous substances. Furthermore, the detection can be done without need for opening containers or otherwise unduly delaying commerce. The process is readily adapted for scanning structural components of buildings and vehicles as well as for scanning the earth at or just below the surface for buried or submerged objects of interest. In contrast to thermal neutron activation analysis techniques, the techniques of the instant invention do not induce high levels of radioactivity in articles being inspected, and accordingly delay time for "cool down" and hazards to personnel are eliminated. Techniques of the present invention are readily adaptable to full automation and computer control and accordingly can provide for high volume/low cost nonvisual identification of the composition of a variety of items. These and other advantages of the instant invention will be apparent from the drawings, description and claims which follow.

BRIEF DESCRIPTION OF THE INVENTION

There is disclosed herein apparatus for the noninvasive inspection of an object so as to determine the presence of at least one preselected element therein. The apparatus comprises: a neutron beam source for generating a beam of neutrons having a preselected energy and directing that beam onto the object, a neutron beam energy controller for varying the energy of the neutron beam over a preselected range in which resonant scattering of the beam by the preselected element will occur, neutron detector means disposed so as to receive neutrons scattered from the object and generate a signal corresponding thereto and analyzer means for analyzing the signal from the detector so as to determine if resonant scattering of the neutron beam by the object has occurred at an energy corresponding to the energy at which resonant scattering by said at least one preselected element occurs. The analyzer is further adapted to provide an alarm indication if the resonant scattering does so correspond, thereby indicating the presence of the preselected element.

In one embodiment, the apparatus is adapted to assess the relative ratios of at least two different elements in the object under interrogation so as to determine if the object includes a material of a preselected class, such as a contraband object. In this embodiment, the neutron beam controller is further adapted to vary the energy of the neutron beam over a preselected range in which resonant scattering of the beam by said at least two different elements will occur, and the analyzer is further adapted to (1) analyze the signal from the detector to determine if resonant scattering by the two elements has occurred and if so, (2) determine the relative ratios of neutrons scattered by the elements, (3) compare the determined ratios with an established range of ratios corresponding to the preselected class of materials and (4) provide an alarm indication if the determined ratios are within that range.

In another particular embodiment, the apparatus further includes a beam scanner adapted to scan the neutron beam across a plurality of scan points on the object and operable in cooperation with the beam energy controller so as to scan each scan point with the preselected range of energies. The energy controller may be adapted to vary the energy of the neutron beam over the range of 0.1 to 4.2 MeV.

The preselected element may include nitrogen and the analyzer may be operative to determine if resonant scattering of the neutron beam occurs as a result of the direction onto the object of neutrons having energy levels selected from the group consisting essentially of: 0.432 MeV, 0.997 MeV, 1.116 MeV, MeV, 2.749 MeV and 3.510 MeV. In those instances where the preselected element is oxygen, the analyzer may be operative to determine if resonant scattering of a neutron beam occurs as a result of the direction onto the object of neutrons having at energy levels selected from the group consisting essentially of 1.312 MeV, 1.907 MeV, 2.888 MeV, and 3.442 MeV. In those instances where the preselected element includes carbon, the analyzer may be operative to determine if resonant scattering of the neutron beam occurs as a result of the direction onto the object of neutrons having at energy levels selected from the group consisting essentially of 2.077 MeV and 2.818 MeV. Similar detections may be made for sulfur at 0.103 MeV; potassium at 0.058 MeV and 0.068 MeV; and beryllium at 0.029 MeV.

In those instances where the ratios of particular elements are being scanned, the two different elements may comprise oxygen and nitrogen in the established range of oxygen-nitrogen ratios corresponding to the preselected class of material may be from 1.0 to 4.0. In other instances, the component atoms may include oxygen, nitrogen and carbon in the established range of ratios for oxygen to nitrogen may be from 1.0 to 4.0 and the established range of ratios of carbon to nitrogen may be from 0 to 3.0.

In yet other instances of ratio analysis, the component atoms may include oxygen, nitrogen and carbon and the established range of oxygen to nitrogen ratios may be from 1 to 5 and the established ratio of carbon to nitrogen ratios may be 16 or greater.

The apparatus may include a neutron shield for assuring that the detector primarily senses neutrons scattered from the object. The apparatus may further include transport means for moving the object being scanned to a scanning station, retaining the object in the scanning station for a predetermined period of time and removing the object from the scanning station. The apparatus may further include means for varying the angle of incidence at which the neutron beam is directed onto the object so as to provide at least two groups of scattered neutrons, each group corresponding to a different angle of incidence. In this embodiment, the analyzer is further adapted to process signals generated by the detector and corresponding to the two groups of back scattered neutrons so as to provide spatial information regarding the location of the preselected element in the object under interrogation. In certain refinements, the angle of incidence may be varied by moving the object relative to the neutron beam whereas in other instances, the beam may be moved relative to the object.

The neutron beam source may include a proton source adapted to provide a beam of protons having a preselected energy, a target disposed in the path of the proton beam for emitting neutrons when bombarded thereby, a collimator disposed between the target and the container and comprising a neutron shield having an aperture therein. The neutron beam energy controller may be operatively connected to the proton source so as to control the energy of the proton whereby the energy of the neutrons produced by the bombardment of the target is also controlled. The target may be fabricated from a material containing an element chosen from the group consisting essentially of lithium, carbon, oxygen, deuterium, tritium, helium and combinations thereof.

In one embodiment adapted to scan the object under interrogation with a neutron beam, the neutron beam source includes a proton beam source for generating a beam of protons having a controllable energy, a plurality of lithium targets for emitting neutrons when bombarded by the beam of protons and a collimating neutron shield disposed between the plurality of lithium targets and the object being inspected. The collimating neutron shield has a plurality of collimating apertures therein, each disposed proximate one of the lithium targets and one of the scan points. The apparatus includes a beam scanner comprised of a proton beam deflection device for electromagnetically deflecting the beam of protons to a selected one of the plurality of lithium targets, and the beam energy controller is operatively connected to the proton source so as to vary the energy of the proton beam whereby the energy of the neutron beam produced thereby is also varied.

In another particular embodiment, the neutron beam energy is controlled so as to provide a short pulse of neutrons and the detector is synchronized with the beam energy controller so as to only sense scattered neutrons produced by that short pulse. In particular embodiments, the neutron beam energy controller may be adapted to continuously vary the energy of the neutron beam over the preselected range, or it may be adapted to vary the energy in a stepwise manner. The apparatus of the present invention may further include an x-ray scanner associated therewith so as to provide a visual display of an x-ray image of the contents of the object under investigation. In one embodiment, the object being interrogated is in a relatively fixed position as, for example, a building or the surface of the earth, and the apparatus of the present invention is deployed in a mobile form adapted to be moved across the object. According to the present invention, there are also taught methods for the nonvisual inspection of an object to determine the presence of at least one preselected element therein.

DETAILED DESCRIPTION OF THE INVENTION

Figure 1:
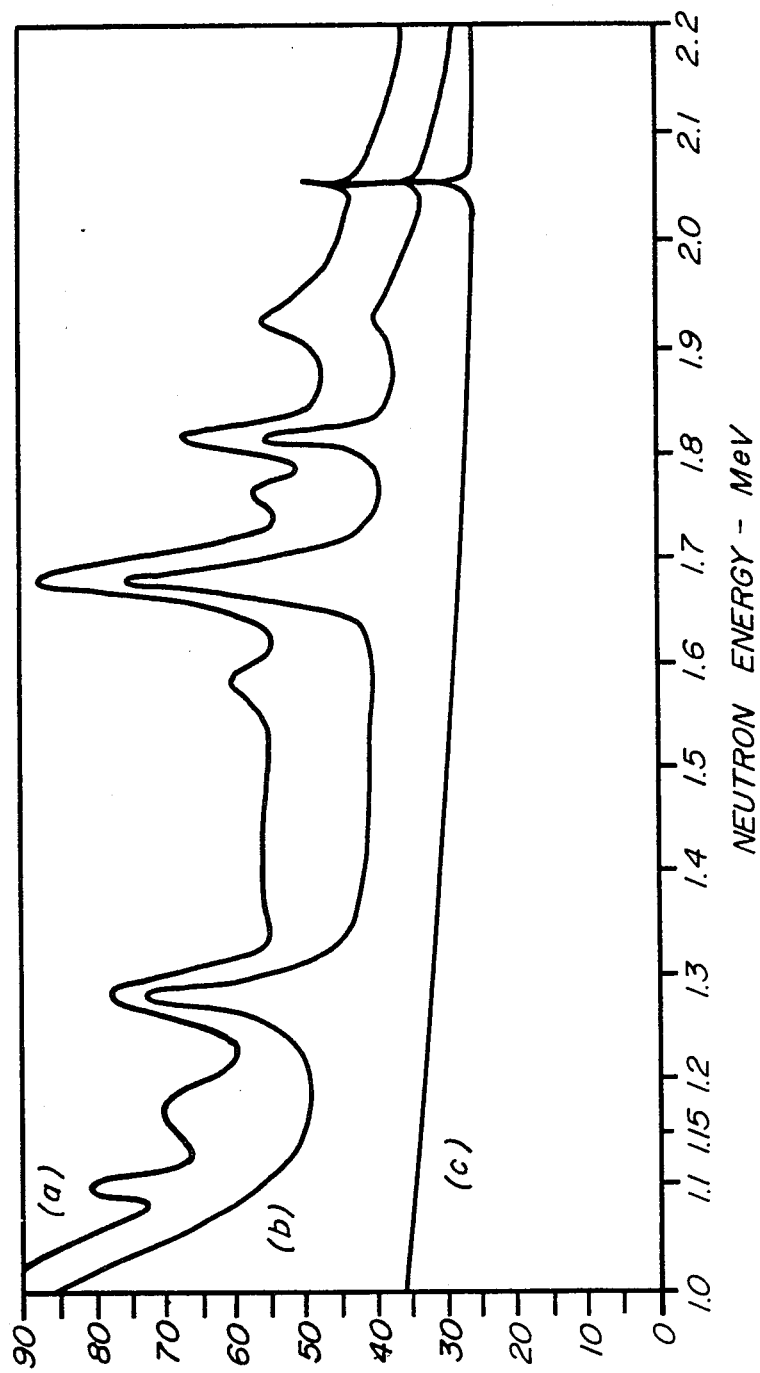
FIG. 1 is a depiction of neutron resonant elastic scatter spectra for (a) an explosive (b) a non-explosive polymer, and (c) a hydrocarbon.

Although briefly discussed previously, the principles of the present invention will be recapitulated. Each element, and in fact each isotope has a unique neutron resonant scattering spectrum and this spectrum can be utilized to determine the composition of materials in closed containers. The technique is basically a spectroscopic analysis and the spectra are obtained by directing a beam of monoenergetic neutrons at an object, and detecting the scattered neutrons. As the energy of the incident neutrons is varied the intensity of the scattered neutrons will change. There are resonance peaks in the scatter spectrum, that is to say neutrons having certain energies are scattered more efficiently from particular atomic species than are neutrons with different energies. The scatter spectrum will thus include one or more maxima corresponding to those points where resonant scattering occurs. For example, oxygen has resonance peaks at approximately 0.434 Mev, 1.312 Mev, 1.907 Mev, 2.888 Mev and 3.442 Mev; nitrogen has resonance peaks at 0.432 Mev 0.997, 1.116 Mev; 2.230 MeV, 2.749 Mev, and 3.510 Mev while carbon exhibits resonances at approximately 2.077 Mev and 2.818 Mev. Additionally, sulfur has a resonance at 0.103 MeV, boron at 0.430 MeV, beryllium at 0.029 and 0.390 MeV, phosphorous at 0.157 MeV, potassium at 0.058 and 0.068 MeV and fluorine at 0.049 MeV. (All of the foregoing data are from Brookhaven National Laboratory Report #325, third edition, and are believed to be accurate. Should the values later be determined to differ, the principles and relationships disclosed herein are still valid.) In addition to these peaks, the resonant scatter spectra of these elements also exhibit many other peaks at different energy levels.

The location of the peaks in the spectrum may be correlated with the atomic species from which scattering is occurring and the absolute magnitude of those peaks may be correlated with the number of scattering nuclei present. By looking for a "signature" spectrum, that is to say a particular peak or group of peaks associated with a given element, the presence as well as the relative quantity of that element can be assessed. By measuring peaks corresponding to different elements, the ratios of particular atoms present in a sample under investigation may be determined. It has been found that items of contraband such as narcotics or explosives have particular ranges of ratios for elements such as carbon, oxygen and nitrogen, which ranges may be utilized as signatures for such materials. For example, it has been found that most explosives have an oxygen to nitrogen ratio within the range of 1.0 to 4.0 and a carbon to nitrogen ratio which is in the range of 0 to 2.5. Disassociating type explosives have a carbon to nitrogen ratio which is between 0 and 0.5 and a hydrogen-nitrogen ratio which is between 0.5 and 2.0. Narcotics in contrast, have an oxygen-nitrogen ratio which is typically in the range of 1 to 5 and a carbon-nitrogen ratio which is 16 or greater.

Problems can occur because certain resonance peaks of particular atoms will overlap and interfere with measurement of other atoms of interest; for example, the 0.432 MeV resonance of nitrogen interferes with the measurement of the 0.434 MeV resonance for oxygen. There are however, many distinctive resonances for each particular nucleus which are free from significant interference particularly if adequate monochromaticity of the neutron source is maintained.

Effective detection of the neutrons will depend upon the monochromaticity, energy range and intensity of the neutron source as well as the sensitivity of the detectors for scattered neutrons. Accordingly, collimation and shielding will be needed at the source and the detectors to attenuate background signals arising from spurious neutrons not scattered by the sample.

Referring now to FIG. 1, there is shown a set of neutron resonant scatter spectra for some particular materials of interest. Curve C is representative of an unsaturated hydrocarbon, namely propylene and as indicated includes only one resonance peak at approximately 2.08 MeV. Curve B is the resonance scatter spectrum of a similar chemical compound which further includes oxygen therein. It will be noted that the spectrum becomes much more complex owing to scattering from oxygen atoms. Curve A is a spectrum for RDX, a common plastic-type explosive. It will be noted that while the compositions of the three materials depicted are relatively similar, the spectrum of the RDX includes particular resonance peaks not found in those of the other compounds. These peaks are correlatable with nitrogen content and may be utilized to establish oxygen-nitrogen ratios and carbon-nitrogen ratios as previously mentioned. From the spectra of FIG. 1 it should be apparent, the manner in which the method in the apparatus of the present invention may be employed to detect contraband substances.

In addition to the use of ratios for analysis, contraband may be more simply detected by analysis of scattered neutrons to determine the presence or absence of particular elements of interest. Since each element has a characteristic scatter spectrum, such spectra may be employed as a fingerprint to detect the presence of elements of interest such as nitrogen.

Figure 2:
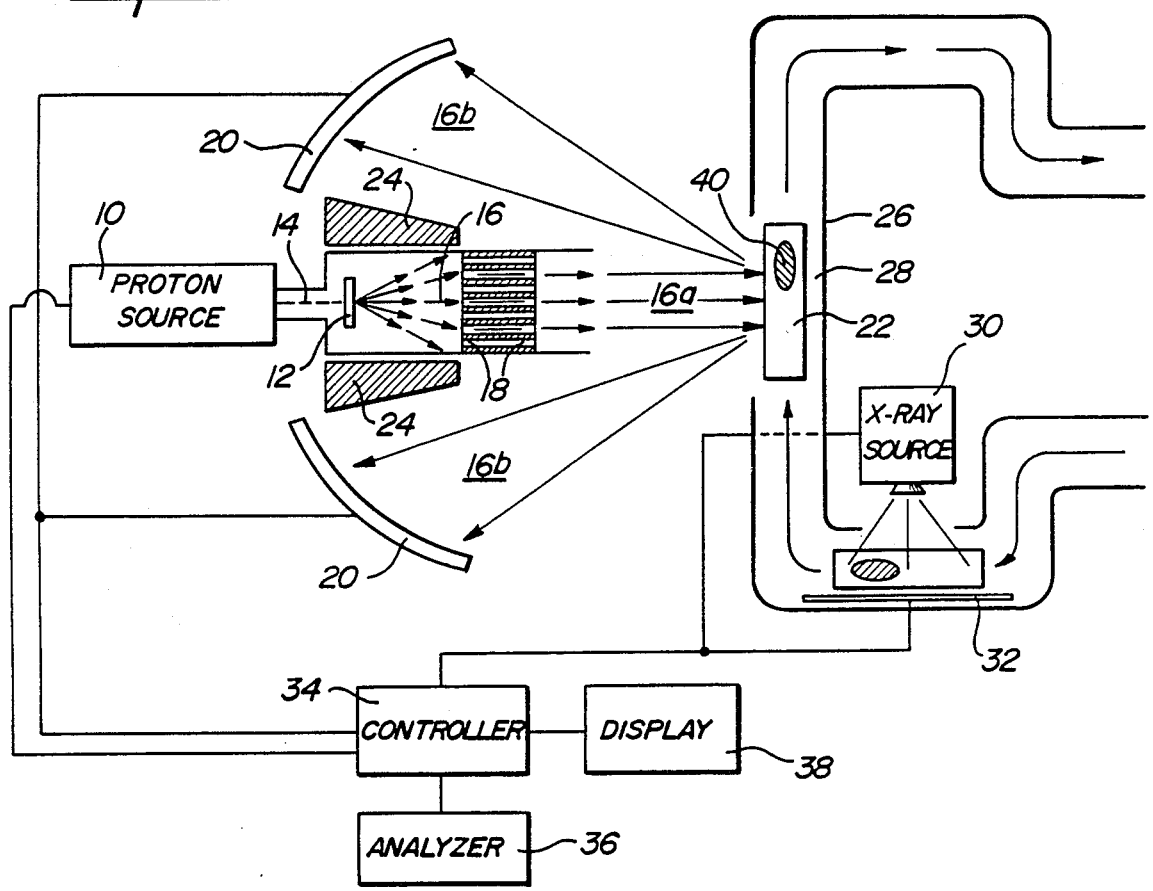
FIG. 2 is a schematic depiction of one particular apparatus structured in accord with the principles of the present invention as disposed to interrogate closed containers to detect the presence of contraband.

Referring now to FIG. 2, there is shown a schematic depiction of one particular contraband detection system structured in accord with the principles of the instant invention. The system of FIG. 2, is adapted to project a beam of neutrons onto an object such as a closed container collect neutrons backscattered therefrom and analyze them to determine the likelihood of contraband being within the closed container.

The system of FIG. 2 includes a neutron source capable of providing neutrons with a varying range of energies. There are many different types of neutron sources available to those with skill in the art. One particularly easy to control source is depicted in FIG. 2 and is comprised of a proton source 10 adapted to bombard a target 12 with a beam of energetic protons 14. The target 12 is fabricated from a material which generates neutrons when struck by protons. Lithium is one such preferred material, although other material such as carbon, oxygen, deuterium, tritium, and helium may be employed as target materials either in the form of pure materials or as compounds thereof, as is known to those of skill in the art.

When bombarded by a proton beam, a lithium atom absorbs a proton and emits a neutron, being converted to beryllium in the process. The energy of the emitted neutron will be a function of the energy of the incident proton and accordingly, neutron beam energy may be controlled by controlling the proton source 10. While the instant invention may be practiced with neutrons having a wide range of energies, it has been determined that for most contraband, the range of approximately 0.1–2.2 MeV will be sufficient, however this range may be readily extended to 4.0 MeV and beyond, particularly when high penetration is required, as for example when the object being interrogated is large or dense. Likewise, for detection of particular elements a lower energy range may be appropriate, particularly since the elastic scatter cross section is larger at lower energies.

It is estimated that if neutron resonant scatter peaks are to be determined with high precision, the energy spread (i.e. monochromaticity) of the neutron beam should be kept to several, i.e., ten KeV; that is to say, the bandwidth of neutron energy should be approximately 10 KeV at the half maximum for each nominal energy level. Since a one KeV energy spread can be readily maintained with presently available sources, the system of the present invention is operating well within the state of the art.

The neutrons 16 emitted by bombardment of the target 12 are generated in a random direction and accordingly the apparatus must include a collimator 18 to define a parallel neutron beam. As depicted, the collimator is a relatively thick body of neutron absorbing material such as polyethylene loaded with boron and including a plurality of elongated channels therethrough. The channels function to permit only those neutrons traveling in approximately parallel paths to pass. Neutron collimators are known to those with skill in the art and there are many designs and materials which may be incorporated herein. For example, instead of the aforementioned polyethylene, the collimator may be a water filled body having channels extending therethrough.

The apparatus of FIG. 2 further includes a pair of neutron detectors 20 disposed so as to receive neutrons backscattered from the object 22 being interrogated. These detectors may for example be scintillation-type detectors as are well known to those of skill in the art. While the embodiment of FIG. 2 utilizes detectors disposed to sense backscattered neutrons, the scattering process is quite isotropic. Therefore, the detectors may be placed in numerous other positions. It is essential, however, that care be taken in the placement of the detectors 20 so as to avoid generation of spurious signals from neutrons other than those scattered from the object 22 under investigation. Accordingly, the apparatus will include appropriately placed and shaped neutron shields 24 disposed so as to absorb significant numbers of stray neutrons.

Rejection of spurious signals and an increase in sensitivity may be achieved by use of a time of flight detection technique wherein the neutron source is operated in a pulsed mode so as to emit short preferably nanosecond bursts of neutrons and the detector 20 is energized in synchrony so as to detect only those neutrons in a particular burst and having a transit time equal to the interval required to travel from the source to the object 22 being interrogated and back to the detector. In this manner neutrons scattered by atmospheric oxygen or nitrogen or by other objects not under interrogation will be rejected.

The inspection system further includes a conveyer 26 for moving objects into position for interrogation. As depicted, the conveyer system 26 is fabricated from a material relatively impervious to neutrons so as to function as a shielding member. The conveyer system includes an interrogation station 28 having an opening through which the neutron beam may pass. The conveyer system 26 is configured to define a tortuous path so as to baffle the flow of neutrons therethrough. In this manner, the insertion and removal of objects into the system is facilitated while eliminating the need for shielding at the exit and entrance regions thereof. In the depicted embodiment, the system further includes means for X-ray scanning of objects along with with neutron interrogation thereof. Toward this end the apparatus includes an X-ray source 30 and an X-ray detector 32 disposed so as to generate an X-ray image of an object concomitant with neutron interrogation.

As depicted, the apparatus is controlled by a controller 34 which, as will be elaborated upon in greater detail herein below, may be a computer or microprocessor. The controller 34 receives inputs from the neutron detectors 20, the proton source 10, the X-ray source 30, the X-ray detector 32 and controls those items in response to such inputs. Also associated with the controller 34 is an analyzer 36, adapted to analyze the signal from the neutron detectors so as to determine the presence of a preselected element and/or the ratios of particular atomic species as indicated by the scatter signal. The controller also has a display device 38, such as a cathode ray tube or the like associated therewith for displaying the results of the inspection. Display may be in the form of alpha-numeric printout indicating the likelihood of contraband being in the container, or the display may comprise a visual display of the contents of the container indicating by color, or alpha-numeric code, regions of suspect content. The controller 34 may be utilized to merge an X-ray image with a neutron generated image in a composite fashion so as to better indicate the content of a package.

In operation of the device of FIG. 2, a beam of protons 14 is generated by the proton source 10 and directed to impinge upon the lithium target 12 so as to generate a beam of neutrons 16. The controller 34 varies the energy of the proton beam 14 in accord with a predetermined program so as to vary the energy of the resultant neutron beam 16. This variation may be in a continuous manner, or may be step-wise over the range of interest. In those instances where the beam energy is varied in a step-wise manner, it will be desired that the steps correspond to at least one particular resonance energy of interest.

Upon bombardment by the proton flux 14, the target 12 emits neutrons 16 which are collimated by the collimator 18. The collimated beam 16a is directed toward the object 22 being interrogated in the interrogation region 28 and that beam 16a impinges upon the object 22 penetrating thereinto and scattering from objects inside. As indicated, the container 22 under interrogation includes therein an item 40 of contraband. Neutrons backscattered from the container 22 rebound and are collected by the detectors 20. It will be appreciated that the scattered beam 16b is generally spherical in shape and accordingly it may be desirable to configure the detectors 20 as a hemispherical or parabolic array.

The detectors 20 produce a signal corresponding to the intensity of neutrons received thereby and this signal is communicated to the controller 34 for analysis by the analyzer 36.

In the analyzer 36 the intensity of the neutron signal is correlated with the energy of the incident neutron beam 16a and this signal utilized to determine the resonant scatter spectrum. This information may be further processed to identify either a single element or to determine relative ratios of elements. Once these ratios are determined, they are compared with ratios for known contraband. If a match is obtained the controller 34, signals the display 38 so as to give an alarm indication.

Obviously, many refinements of the foregoing technique will be apparent to one of skill in the art. For example, sensitivity of the system may be increased by operation in a pulsed or time of flight mode as previously discussed whereby neutron energy is directed onto the container 22 in short bursts. The operation of the detectors 20 is synchronized with these bursts so that the detectors 20 only sense neutrons produced by the bursts and scattered from the container. In this manner, spurious signals from residual radiation, neutrons scattered by the atmosphere and the like do not interfere with operation of the system thereby increasing sensitivity. In other variations, the transport system 26 may include additional stations for visual or magnetic scanning of parcels and may also include "cool down"

sections to allow for decay of any residual radiation induced by the neutron beam, although in a system of this type employing elastic scattering rather than absorption of neutrons, such residual radiation will be minimal.

Relatively small objects may be interrogated in their entirety by a single beam of neutron energy however, in the instance of larger objects it may be desirable to obtain a spatial resolution of the contents so as to pinpoint the exact location of the suspect contraband. One method of obtaining such positional information involves scanning the neutron beam across the surface of the object under interrogation. There are many methods for such scanning. The simplest would involve utilizing a fixed, relatively small diameter neutron beam and moving the object across the beam as for example in an X-Y coordinate matrix. Another variation of this system would involve mechanically moving the neutron source so as to scan the neutron beam across the object.

Figure 3:
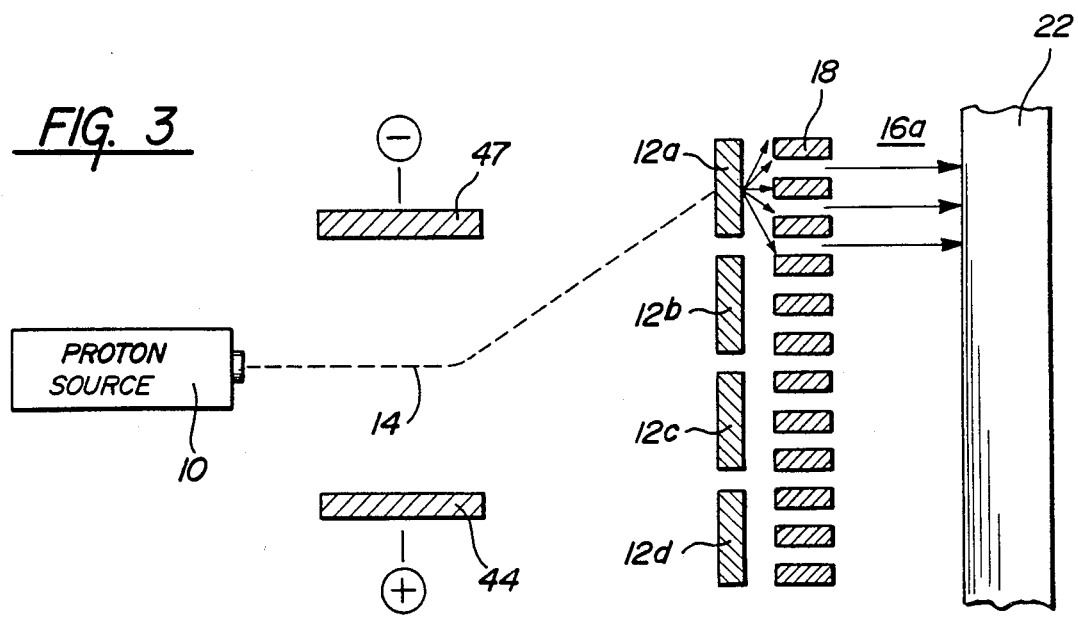
FIG. 3 is a schematic depiction of a neutron beam source as adapted to scan the surface of a closed container.

Referring now to FIG. 3 there is disclosed an alternative method for scanning a neutron beam. This method is electronic and hence allows for a very rapid beam scan. As disclosed in the figure, a proton source 10, generally similar to that previously described is employed to generate a proton beam 14, which beam is steered by a pair of electrode plates 47, 44. The scanning system further includes a plurality of targets 12a, 12b, 12c, 12d generally similar to those previously described. Each target has a collimator 18 proximate thereto. In this manner, each target is a separate neutron generating system adapted to generate a relatively small area neutron beam 16a when struck by a proton beam 14. As should be apparent, the neutron beam 16a can be swept across the surface of the object 22 being interrogated by simply steering the proton beam 14 from one target to another. For example, in the apparatus of FIG. 3, the charge on the two electrode plates 47, 44 is varied so as to sweep the proton beam 14 from plate 12a down to plate 12d and in so doing the neutron beam 16a is swept across the surface of the object 22 being scanned.

In order to provide for the capability of X-Y matrix scanning a matrix of small targets 12 can be arrayed in a plane and a second set of control electrodes generally similar to the first set 47, 44 is employed to sweep the proton beam 14 across the matrix of targets.

It should be kept in mind that as the neutron beam is being scanned the energy thereof will have to be varied if a resonance spectrum is to be obtained. This variation of energy may be carried out for each scan point individually, that is to say the beam 14 may be directed onto a first target, as for example target 12a and the full range of energies under investigation accessed at that time; and the beam may then be moved onto the adjacent target. In another embodiment, each of the targets in the array is swept with a first level of proton energy and then sequentially swept with succeeding energy levels. The choice of operational mode will depend upon processing software employed.

Figure 6:
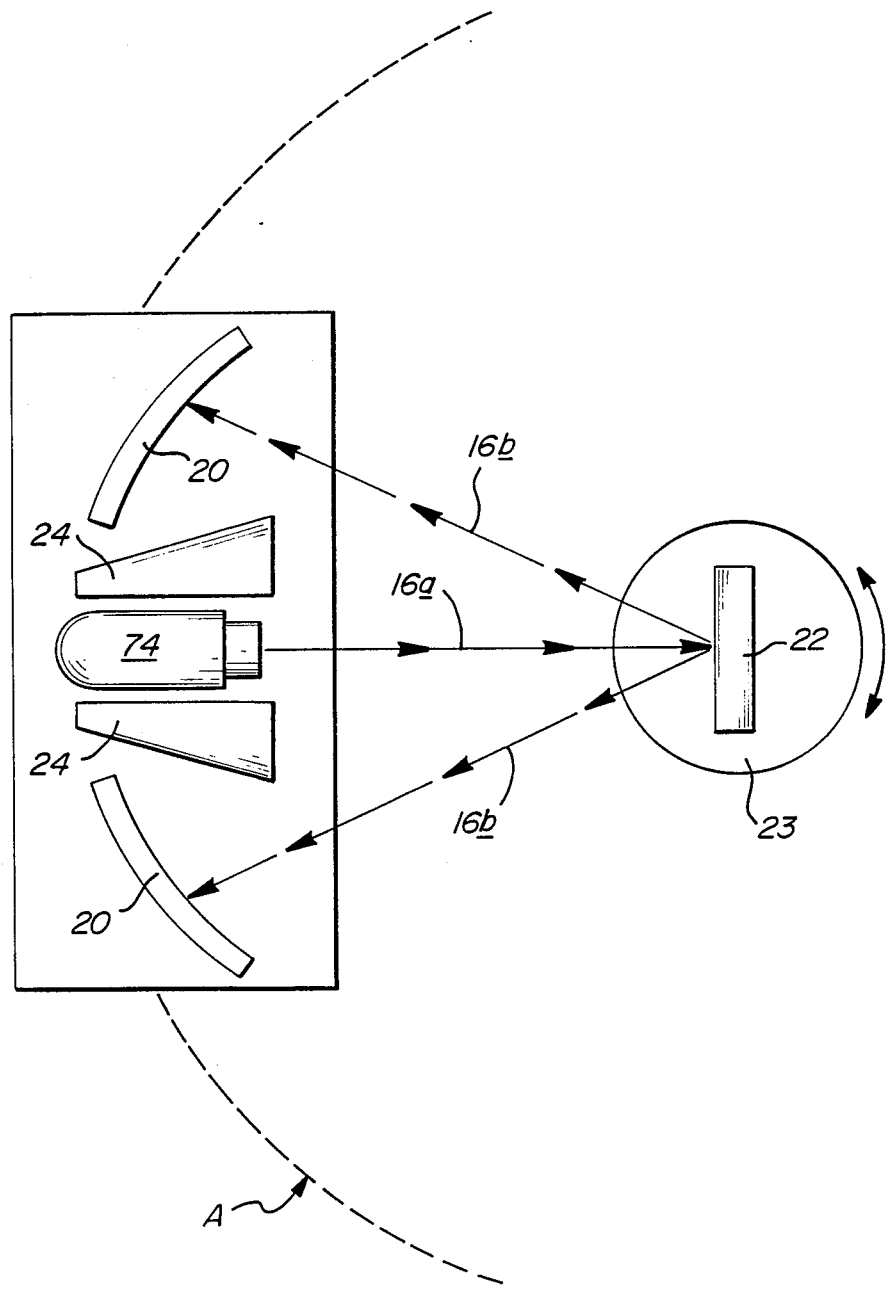
FIG. 6 is a schematic depiction of one embodiment of apparatus of the present invention wherein the object and/or the neutron beam source may be repositioned relative to one another.

The system of the present invention may be readily modified to give three-dimensional information indicating, for example, the shape and/or position of suspect material within an object being investigated as illustrated in FIG. 6. In light of the disclosure herein, such modifications should be readily apparent to those of skill in the art and accordingly constitute a part of the present invention. Such three-dimensional information may be obtained, for example, by obtaining a first neutron signal with the object in a first orientation relative to the neutron beam and subsequently obtaining at least one more signal after the object and beam have been rotated relative to one another. Such rotation can be expediently accomplished by utilizing a movable support (as shown at 23 in FIG. 6) for the object 22 under interrogation or alternatively, by moving the neutron beam and/or detector relative to the object. Once a plurality of such measurements have been made from differing perspectives, they may be combined electronically utilizing well-known image processing techniques so as to give three-dimensional information about the contents of the object.

Tomographic techniques have been well developed for use with X-ray and ultrasound imagers, and such techniques are readily adaptable for use with the technology disclosed herein. Tomographic information may be obtained in either a backscatter or forward scatter mode as is well-known to those of skill in the art. For example as shown at 23 in FIG. 6, a detector 20 and neutron source 74 may be mounted so as to rotate in an arc about the object 22, which is maintained at the center of the arc and through the use of appropriate processing software a series of tomographic images generated; likewise, the detector and neutron source may be in a fixed position and the object rotated. In accord with the other well-known principles, the object may be interrogated so as to produce a stereoscopic type of image by generating a pair of images taken from different points of view as for example, by shifting the object to the right or left relative to the incident neutron beam.

While the principles of the instant invention have primarily been described with reference to a stationary apparatus for interrogating objects, the present invention may be readily adapted to provide a mobile apparatus. Apparatus of this type may be utilized to scan relatively large objects so as to detect the presence of hidden or otherwise inaccessible materials therein.

Figure 5:
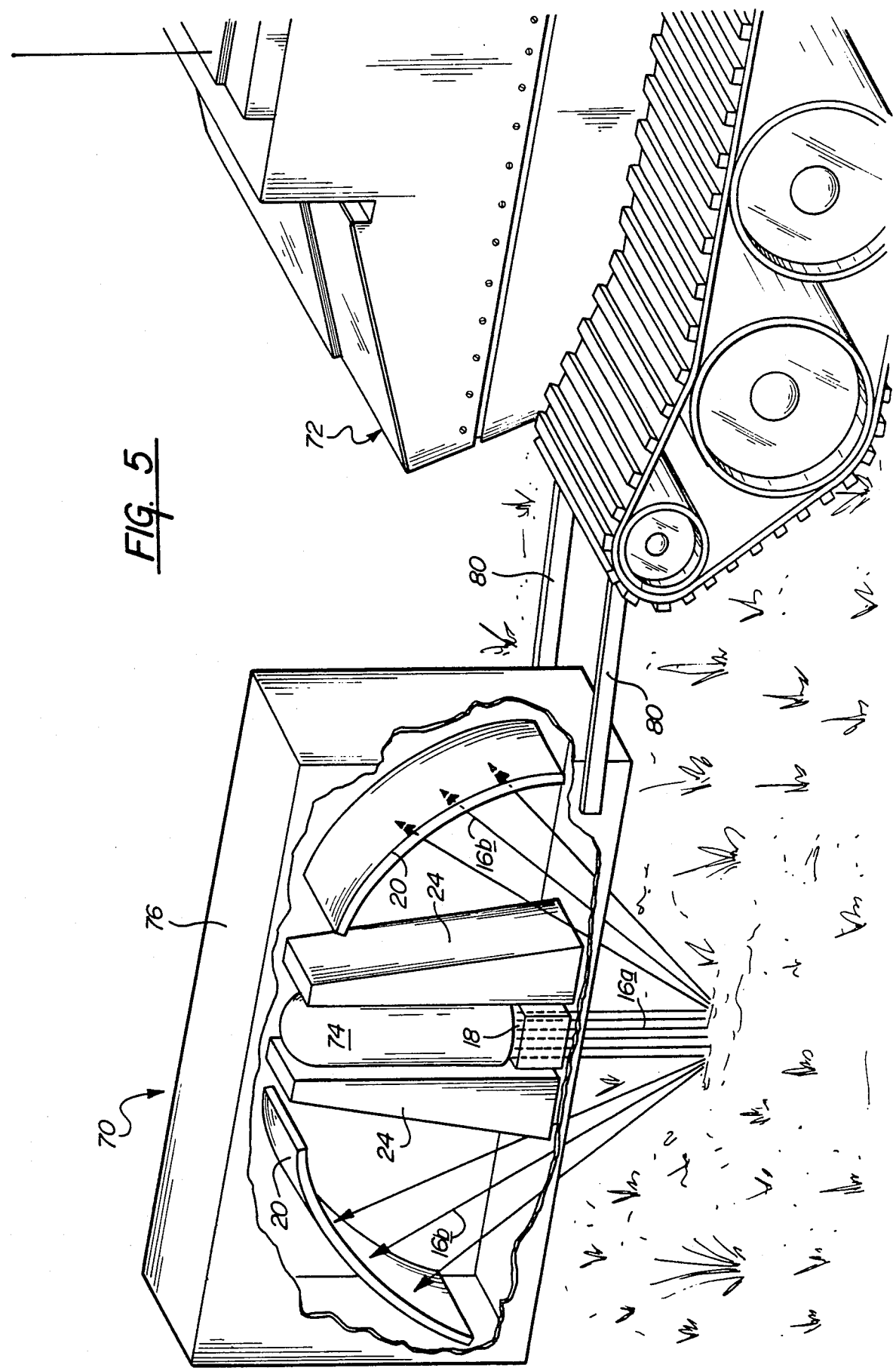
FIG. 5 is a depiction of one particular mobile form of the apparatus of the present invention as deployed to locate subterranean explosive devices.

Referring now to FIG. 5, there is shown one such embodiment of mobile scanning apparatus 70, utilized as a mine sweeping apparatus and deployed in conjunction with a tracked vehicle such as an armored personnel carrier 72.

The apparatus 70 of FIG. 5 is a portable version of the apparatus described with reference to FIG. 2 and as such, like structures will be referred to by similar reference numerals. The apparatus 70 of FIG. 5 includes a neutron source 74 having a collimator 18 associated therewith. The source and collimator cooperate to provide a relatively collimated beam of neutrons 16a directed toward the object being interrogated, in this case the surface of the earth. The apparatus further includes a pair of neutron detectors 20 generally similar to those previously described as well as neutron shielding 24 for attenuating stray signals which may reach the detector. The apparatus is housed within a container 76 shown here in cutaway view and having an opening in the bottom, not generally visible, through which the neutrons pass. It is normally preferred that the container 76 be fabricated from a neutron absorbing material so as to limit the release of stray neutrons.

It is generally preferred in a mobile apparatus of this type to remove the controller, analyzer and display from the immediate vicinity of the apparatus 70 itself and this is expediently accomplished by the use of a connecting cable or wireless data link which conveys the signals produced by the detectors 20 to remote locations for processing. As shown in this embodiment, the apparatus 70 is mounted upon a tracked vehicle 72 by means of a pair of mounting brackets 80, although obviously other such configurations may be employed.

In operation, the vehicle 72 having the apparatus 70 mounted on the front end thereof is driven across a field. The neutron source 74 projects a beam of collimated neutrons 16a onto and into the surface of the subjacent earth. Neutrons resonantly scattered from objects in the earth are captured by the detectors 20 and the signals produced thereby are processed so as to identify a resonant spectrum. Various signal processing schemes previously described may be employed in conjunction with such an embodiment, for example, ratio analysis may be utilized to precisely identify subjacent articles. However, in the instance of mine detection, it will generally be found most expedient to simply scan for large amounts of nitrogen, an element not normally found in significant amounts in the subsurface of the earth and generally indicative of explosives. A simplified apparatus may be constructed wherein the energy of the neutron beam 16a is varied in a stepwise manner over a range in which a particularly strong nitrogen resonance will occur. For example, the beam 16a may be pulsed between one of the strong nitrogen resonances, as for example 1.116 MeV and a point wherein nitrogen resonance does not occur such as for example 1.2 MeV. Indication of a relatively strong signal at a resonance point vis a vis, the non-resonance point will be taken as in indication of high nitrogen concentration. Obviously, the "off resonance" energy level must be one which will not correspond to resonance scattering by compounds normally found in soil such as water or minerals.

It may, in some instances, be desirable to employ relatively energetic neutrons, as for example 2-4 MeV or higher neutrons to enable the beam to probe deep into the subjacent earth. Such deep probing is particularly useful in searching for buried caches of explosives in underground bunkers or the like. A mine sweeping apparatus of the type described in FIG. 5 is particularly advantageous insofar as it is well adapted to find nonmetallic explosive devices. As depicted, the neutron beam 16a is shown as being relatively narrow; obviously, it is desirable to sweep the entire path of the vehicle 72, and accordingly, the apparatus 70 will be "swept" back and forth in the vehicle's path. Alternatively, the neutron source 74 will be adapted to provide a wider beam. Although the detector apparatus 70 of FIG. 5 is depicted as disposed to detect mines directly therebeneath, it may be advantageous to orient that apparatus 70 to project the neutron beam 16a forward of itself and into the earth. In this manner, the mines will be detected well in advance of the apparatus and vehicle, thereby preventing damage in the event that a mine is detonated as for example by the neutron beam or the presence of the vehicle.

Variations of the FIG. 5 apparatus may be constructed for other particular purposes. For example, the portable scanning apparatus 70 may be particularly configured to sense narcotic material and may be deployed to scan vehicles for the presence of hidden contraband therein. The apparatus may be further modified so as to be carried by a helicopter or other aircraft so as to rapidly scan buildings, water vessels and densely forested areas for mines or caches of narcotics and/or explosives. In the event that aerial scanning is utilized, use of time of flight detection techniques is considered particularly important. In a typical aerial detection mode it is anticipated that the detector will be at least 10-20 meters above the earth consequently the intervening atmosphere will present a large volume of nitrogen to the neutron beam. Use of time of flight techniques will allow for rejection of neutrons scattered by this nitrogen. These and numerous other such modifications should be readily apparent in light of the foregoing description and drawings.

Figure 4:
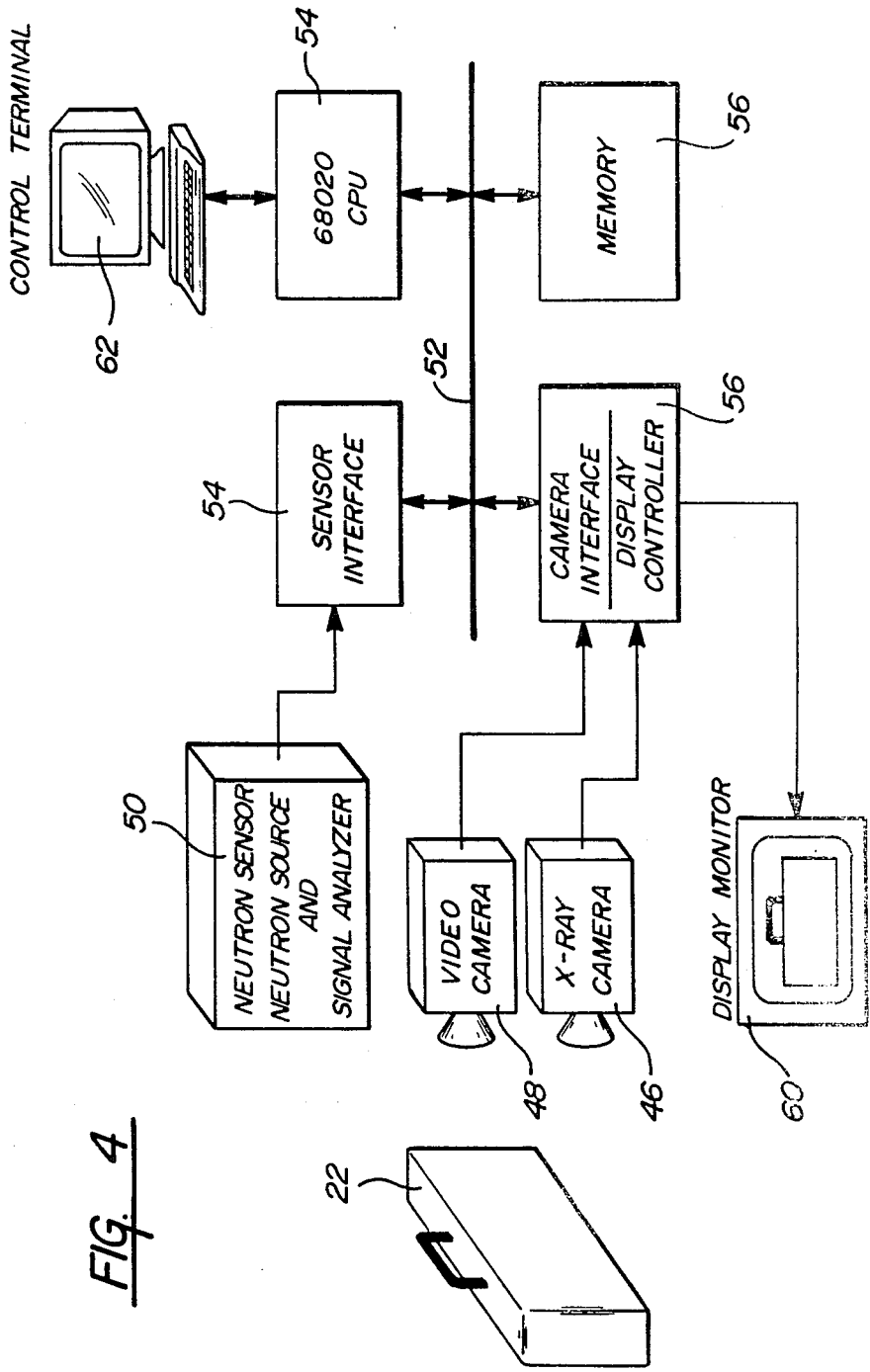
FIG. 4 is a schematic diagram of the processor architecture for a neutron backscatter inspection system of the present invention.

There are obviously many arrangements of processor architecture that may be employed in conjunction with the operation of the scanning system of the present invention. FIG. 4 depicts the processor architecture for one such embodiment adapted for use with the FIG. 2 apparatus. As shown in the figure, the object 22 is scanned either simultaneously or sequentially by an X-ray camera 46, a video camera 48 and a neutron apparatus 50. The neutron apparatus 50 is generally similar to the system previously described and includes source, sensor and analyzer. The signal from the neutron apparatus 50 is communicated to a VME data bus 52, via a sensor interface 54 which is adapted to buffer and time the signal. The bus 52 carries the signal to a central image processor such as A 68020 CPU unit, or a CYTO ® computer 54 for analysis.

The signals from the video camera 48 and X-ray camera 46 are conveyed to the camera interface/display controller 56 which buffers and conditions those signals and also carries them to the data bus 52. In the central processor 54, the various signals are analyzed, compared with data from memory 56, reformatted and restored in memory. The central processor 54 configures and combines the input signal so as to produce a display signal carried to the display controller 56 via the data bus 52. The display controller 56 activates a display monitor 60 to display information generated by the system.

The display monitor may be a cathode ray or liquid crystal type display and may be configured to display overlayed visible and x-ray images together with a signal indicating location of suspect contraband. Access to the various functions of the system is preferably via a user-operated control terminal 62 having keyboard or other input device and a display device such as a cathode ray tube associated therewith.

This display capability may be employed in an inspection process analogous to x-ray inspection; however, the particular sensitivity of the technique for low atomic weight elements eliminates the difficulties encountered in applying x-ray inspection techniques for particular tasks. For example, it is desirable to nondestructively visualize explosive bodies within bombs, artillery projectiles and the like, for purposes of quality control. However, the explosive material is of low molecular weight and not readily visualized by x-rays. The present invention readily images such material allowing for accuate, non-invasive inspection.

While the foregoing description has been primarily oriented toward an imaging embodiment, it should be appreciated that the system may be simplified to give a visible or audible alarm if a material of interest is detected. Such an embodiment will be sufficient for most rapid screening systems, and may be used as a prescreen prior to utilizing a full imaging embodiment of the invention.

The foregoing drawings, description and discussion are meant to be illustrative of the principles of the present invention and not meant to be limitations upon the practice thereof. Obviously, many variations will be apparent to those skilled in the art in light of the foregoing. Accordingly, it is the following claims, including all equivalents, which define the scope of the present invention.

I claim:

1. Apparatus for the noninvasive inspection of an object so as to determine the presence of at least one preselected element therein, said apparatus comprising:
   a neutron beam source for generating a beam of neutrons having a preselected energy and directing the beam onto the object;
   a neutron beam energy controller for varying the energy of the neutron beam over a preselected range, in which resonant scattering of the beam by said at least one preselected element will occur;
   neutron detector means disposed so as to receive neutrons scattered from the object and generate a signal corresponding thereto; and
   analyzer means for (1) analyzing the signal from said detector so as to determine if resonant scattering of the neutron beam by the object has occurred at an energy corresponding to resonant scattering by said at least one preselected element, and (2) providing an alarm indication if the resonant scattering of the neutron beam so corresponds, such that the presence of said at least one preselected element is indicated.

2. Apparatus as in claim 1, further adapted to determine the presence and relative ratios of at least two different elements in said object so as to determine if the object includes a material of a preselected class, wherein:
   the neutron beam controller is further adapted to vary the energy of the neutron beam over a preselected range in which resonant scattering of the beam by said at least two different elements will occur; and
   the analyzer is further adapted to (1) analyze the signal from the detector to determine if resonant scattering by said at least two elements has occurred and if so, (2) determine the relative ratios of neutrons scattered by the elements, (3) compare the determined ratios with an established range of ratios corresponding to said preselected class of materials, and (4) provide an alarm indication if the determined ratios are within the range.

3. An apparatus as in claim 2, wherein said at least two different elements comprise oxygen and nitrogen and wherein the established range of oxygen-nitrogen ratios corresponding to said preselected class of material is from 1.0 to 4.0.

4. An apparatus as in claim 2, wherein said at least two different component atoms include oxygen, nitrogen and carbon and wherein the established range of ratios for oxygen to nitrogen is from 1.0 to 4.0; and wherein the established range of ratios of carbon to nitrogen is from 0 to 2.5.

5. As apparatus as in claim 2, wherein said at least two component atoms include oxygen, nitrogen and carbon and wherein the established range of oxygen to nitrogen ratios is from 1 to 5; and wherein the established range of carbon to nitrogen ratios is 16 or greater.

6. Apparatus as in claim 1, further including:
   a beam scanner adapted to scan the neutron beam across a plurality of scan points on said object, said scanner operable in cooperation with said beam energy controller to scan each of said scan points with said preselected range of energies.

7. An apparatus as in claim 6, wherein said beam scanner is adapted to sequentially scan the neutron beam across the entirety of the object in a two-dimensional matrix such that the entirety of the object is scanned.

8. An apparatus as in claim 6, wherein:
   said neutron beam source includes a proton beam source for generating a beam of protons having a
   analyzing the signal comprises (1) determining if resonant scattering by said at least two elements has occurred and if so, (2) determining the relative ratios of neutrons scattered by the elements, (3) comparing the determined ratios with an established range of ratios corresponding to said preselected class of materials; and wherein,
   providing said alarm comprises providing an alarm if the determined ratios are within the range.

9. An apparatus as in claim 1, wherein said energy controller is adapted to vary the energy of the neutron beam over the range of 0.1 to 2.2 MeV.

10. An apparatus as in claim 1, wherein said energy controller is adapted to vary the energy of the neutron beam over the range of 2.0 to 4.2 Mev.

11. Apparatus as in claim 1, wherein said at least one preselected element includes nitrogen, and wherein said analyzer is operative to determine if resonant scattering of the neutron beam occurs as a result of the direction onto the object of neutrons having energy levels selected from the group consisting essentially of: 0.432 MeV, 0.997 MeV, 1.116 MeV, 2.230 MeV, 2.749 MeV and 3.510 Mev.

12. Apparatus as in claim 1, wherein said at least one preselected element includes oxygen, and wherein said analyzer is operative to determine if resonant scattering of the neutron beam occurs as a result of the direction onto the object of neutrons having energy levels selected from the group consisting essentially of: 1.312 Mev, 1.907 MeV, 2.888 MeV and 3.442 MeV.

13. Apparatus as in claim 1, wherein said at least one preselected element includes carbon, and wherein said analyzer is operative to determine if resonant scattering of the neutron beam occurs as a result of the direction onto the object of neutrons having energy levels selected from the group consisting essentially of: 2.077 MeV and 2.818 MeV.

14. An apparatus as in claim 1, further including a neutron shield disposed so as to shield the detector means from ambient neutrons such that the detector primarily senses neutrons scattered from the object.

15. An apparatus as in claim 1, further including transport means for: (a) moving the object to a scanning station for direction of the neutron beam thereonto; (b) retaining said object in said scanning station for a predetermined period of time; and (c) removing said object from said scanning station.

16. An apparatus as in claim 1, further including:
   means for varying the angle of incidence at which said neutron beam is directed onto said object so as to provide at least two groups of scattered neutrons, each group corresponding to a different angle of incidence; and
   wherein said analyzer is further adapted to process the signals generated by said detector and corresponding to said two groups of backscattered neutrons so as to provide spatial information regarding the location of said at least one preselected element in said object.

17. Apparatus as in claim 16, wherein said means for varying the angle of incidence includes means for moving the object relative to the neutron beam.

18. Apparatus as in claim 16, wherein said neutron beam source and said detector are adapted to move in synchrony relative to the object.

19. An apparatus as in claim 1, wherein said neutron beam source includes:
a proton source adapted to provide a beam of protons having a preselected energy;
a target disposed in the path of said proton beam for emitting neutrons when bombarded thereby; and
a collimator disposed between the target and the object, said collimator comprising a neutron shield having an aperture therein;
and wherein said neutron beam energy controller is operatively connected to the proton source so as to control the energy of said protons such that the energy of the neutrons produced by the bombardment of the target is also controlled.

20. An apparatus as in claim 19, wherein said target is fabricated from a material containing an element chosen from the group consisting essentially of: lithium, carbon, oxygen, deuterium, tritium, helium and combinations thereof.

21. An apparatus as in claim 1, wherein said beam energy controller is adapted to (a) control the neutron beam source so as to generate a short pulse of neutrons and (b) communicate with said detector means so as to synchronize the operation of said detector with the generation of said short pulse of neutrons such that the detector only senses scattered neutrons from said short pulse.

22. An apparatus as in claim 1, wherein said neutron beam energy controller is adapted to continuously vary the energy of the neutron beam over said preselected range.

23. An apparatus as in claim 1, wherein said neutron beam energy controller is adapted to vary the energy of said neutron beam in a stepwise manner over said preselected range.

24. An apparatus as in claim 1, further including an x-ray scanner adapted to provide a visual display of an x-ray image of the contents of said object.

25. An apparatus as in claim 24, wherein said alarm indication is displayed in conjunction with said visual display.

26. Apparatus as in claim 1, wherein said object is in a relatively fixed positional relationship and wherein said apparatus is adapted to be moved across the object.

27. A method for the nonvisual inspection of an object to determine the presence of at least one preselected element therein including the steps of:
directing a beam of neutrons onto the object;
varying the energy of said neutron beam over a preselected energy range in which resonant scattering of the beam by said at least one element will occur;
detecting the scattered neutrons and generating a signal corresponding thereto;
analyzing the signal to determine if resonant scattering of the neutron beam by the object has occurred at an energy corresponding to resonant scattering by said at least one preselected element; and
providing an alarm indication if the resonant scattering so corresponds.

28. A method as in claim 27, further adapted to determine the presence and relative ratios of at least two different elements in said object so as to determine if the object includes material of a preselected class, wherein:
the step of varying the energy of the neutron beam over a preselected range comprises varying the energy over a range in which resonant scattering by said at least two different elements will occur;
analyzing the signal comprises (1) determining if resonant scattering by said at least two elements has occurred and if so, (2) determining the relative ratios of neutrons scattered by the elements, (3) comparing the determined ratios with an established range of ratios corresponding to said preselected class of materials; and wherein,
providing said alarm comprises providing an alarm if the determined ratios are within the range.

29. A method as in claim 27, wherein the step of directing the neutron beam onto the object includes the further step of scanning said beam across a plurality of scan points on said object, and the step of varying the energy of said beam includes varying said energy in cooperation with the scanning of the beam such that each of said scan points is scanned with said preselected range of energy.

30. A method as in claim 29, wherein the step of scanning the beam across a plurality of scan points comprises sequentially scanning the beam across the entirety of the object in a two dimensional matrix such that the entirety of the object is scanned.

31. A method as in claim 27, wherein the step of varying the energy of the beam includes varying the energy over the range of 2.0 to 4.2 Mev.

32. A method as in claim 27, wherein the step of varying said energy comprises varying said energy over a range in which the resonant scattering of neutrons by carbon, oxygen and nitrogen occurs.

33. A method as in claim 32, wherein the step of providing an alarm comprises providing said alarm if the determined ratio of oxygen to nitrogen is in the range of 1.0 to 4.0.

34. A method as in claim 32, wherein the step of providing an alarm comprises providing said alarm if the determined ratio of oxygen to nitrogen is in the range of 1.0 to 4.0 and the determined ratio of carbon to nitrogen is in the range of 0 to 2.5.

35. A method as in claim 32, wherein the step of providing an alarm comprises providing said alarm if the determined ratio of oxygen to nitrogen is in the range of 1 to 5 and the determined ratio of carbon to nitrogen is 16 or greater.

36. A method as in claim 27, wherein the step of varying the energy of the beam includes varying said energy over the range of 0.1 to 2.2 MeV.

37. A method as in claim 27, wherein the step of directing a beam of neutrons onto the object comprises directing a collimated beam of neutrons onto the object.

38. A method as in claim 27, including the further steps of: controlling the beam of neutrons so as to generate at least one short pulse thereof; and, activating detector means in synchronization with the generation of said at least one short pulse so as to detect only scattered neutrons from said pulse.

39. A method as in claim 27, wherein the step of varying the energy of the neutron beam comprises continuously varying the energy of the neutron beam over said preselected range.

40. A method as in claim 27, wherein the step of varying the energy of the neutron beam comprises varying the energy of said beam in a step-wise manner over the preselected range.

41. A method as in claim 27, including the further step of providing a visual display of an x-ray image of the contents of the object.

42. A method as in claim 41, wherein the step of providing an alarm indication comprises providing said indication in conjunction with said visual display.

43. A method as in claim 27, wherein the step of directing the neutron beam comprises directing the beam onto the object from at least two different angles of incidence so as to provide at least two groups of scattered neutrons, and wherein:

the step of analyzing the signal comprises analyzing the signal from each of said at least two groups of scattered neutrons so as to provide spatial information regarding the location of said at least one element in the object.

44. A method as in claim 27, wherein said at least one preselected element includes nitrogen and wherein the step of analyzing the signal comprises analyzing the signal to determine if resonant scattering has occurred as a result of directing a beam of neutrons onto the object having an energy level chosen from the group consisting essentially of: 0.432 MeV; 0.997 MeV; 1.116 Mev; 2.230 Mev; 2.749 Mev; and 3.510 Mev.

45. A method as in claim 27, wherein said at least one preselected element includes oxygen and wherein the step of analyzing the signal comprises analyzing the signal to determine if resonant scattering has occurred as a result of directing a beam of neutrons onto the object having an energy level chosen from the group consisting essentially of: 1.312 MeV; 1.907 MeV; 2.888 MeV; and 3.442 MeV.

46. A method as in claim 27, wherein said at least one preselected element includes carbon and wherein the step of analyzing the signal comprises analyzing the signal to determine if resonant scattering has occurred as a result of directing a beam of neutrons onto the object having an at energy level chosen from the group consisting essentially of: 2.077 MeV and 2.818 MeV.

47. A method as in claim 27 wherein said at least one preselected element includes sulfur and wherein the step of analyzing the signal comprises analyzing the signal to determine if resonant scattering has occurred as a result of directing a beam of neutrons onto the object having an energy level of 0.103 MeV.

48. A method as in claim 27, wherein said at least one preselected element includes potassium and wherein the step of analyzing the signal comprises analyzing the signal to determine if resonant scattering has occurred as a result of directing a beam of neutrons onto the object having an energy level chosen from the group consisting essentially of 0.058 MeV and 0.068 MeV.

49. A method as in claim 27 wherein said at least one preselected element includes beryillium and wherein the step of analyzing the signal comprises analyzing the signal to determine if resonant scattering has occurred as a result of directing a beam of neutrons onto the object having an energy level of 0.029 MeV.

* * * * *

UNITED STATES PATENT AND TRADEMARK OFFICE
CERTIFICATE OF CORRECTION

PATENT NO. : 4,864,142

DATED : September 5, 1989

INVENTOR(S) : Gomberg

It is certified that error appears in the above-identified patent and that said Letters Patent is hereby corrected as shown below:

Column 6, line 63, "1.116 MeV, MeV," should be --1.116 MeV, 2.230 MeV,--.

Column 18, line 9-17, Claim 8 reads

"8. An apparatus as in claim 6, wherein:

said neutron beam source includes a proton beam source for generating a beam of protons having a analyzing the signal comprises (1) determining if resonant scattering by said at least two elements has occurred and if so, (2) determining the relative ratios of neutrons scattered by the elements, (3) comparing the determined ratios with an established range of ratios corresponding to said preselected class of materials; and wherein, providing said alarm comprises providing an alarm if the determined ratios are within the range." and it should read --8. An apparatus as in claim 6, wherein:

UNITED STATES PATENT AND TRADEMARK OFFICE
CERTIFICATE OF CORRECTION

PATENT NO. : 4,864,142

DATED : September 5, 1989

INVENTOR(S) : Gomberg

It is certified that error appears in the above-identified patent and that said Letters Patent is hereby corrected as shown below:

said neutron beam source includes a proton beam source for generating a beam of protons having a controllable energy, a plurality of lithium targets for emitting neutrons when bombarded by said beam of protons and a collimating neutron shield disposed between said plurality of lithium targets and the object, said collimating neutron shield having a plurality of collimating apertures therein, each aperture disposed proximate one of said lithium targets and one of said scan points; and wherein, said beam scanner includes a proton beam deflection device for electromagnetically deflecting said beam of protons to a selected one of said plurality of lithium targets; and wherein, said beam energy controller is operatively connected to the proton source so as to vary the energy of said proton beam such that the energy of the neutron

UNITED STATES PATENT AND TRADEMARK OFFICE
CERTIFICATE OF CORRECTION

PATENT NO. : 4,864,142

DATED : September 5, 1989

INVENTOR(S) : Gomberg

It is certified that error appears in the above-identified patent and that said Letters Patent is hereby corrected as shown below:

beam produced thereby is also varied.--.

Signed and Sealed this

Fourth Day of September, 1990

Attest:

HARRY F. MANBECK, JR.

*Attesting Officer*  *Commissioner of Patents and Trademarks*